US012257410B2

(12) United States Patent
Mansell (10) Patent No.: US 12,257,410 B2
(45) Date of Patent: Mar. 25, 2025

(54) KIT FOR CREATING DISPOSABLE DILATORS AND METHOD FOR THE USE THEREOF

(71) Applicant: Lauren Mansell, Frankfort, IL (US)

(72) Inventor: Lauren Mansell, Frankfort, IL (US)

( * ) Notice: Subject to any disclaimer, the term of this patent is extended or adjusted under 35 U.S.C. 154(b) by 902 days.

(21) Appl. No.: 17/350,337

(22) Filed: Jun. 17, 2021

(65) Prior Publication Data

US 2021/0393931 A1 Dec. 23, 2021

Related U.S. Application Data

(60) Provisional application No. 63/042,744, filed on Jun. 23, 2020.

(51) Int. Cl.
*F25C 1/22* (2018.01)
*A61F 7/12* (2006.01)
*A61M 29/00* (2006.01)
*F25C 1/24* (2018.01)

(52) U.S. Cl.
CPC .............. *A61M 29/00* (2013.01); *A61F 7/12* (2013.01); *A61F 7/123* (2013.01); *F25C 1/22* (2013.01); *A61M 2207/00* (2013.01); *A61M 2209/088* (2013.01); *A61M 2210/1475* (2013.01)

(58) Field of Classification Search
CPC .............. A61M 29/00; A61M 2207/00; A61M 2207/10; A61M 2210/1475; F25C 1/22; F25C 1/24; F25C 1/243; B29C 39/10
USPC ............................................................ 5/632
See application file for complete search history.

(56) References Cited

U.S. PATENT DOCUMENTS

| 2,505,947 | A | * | 5/1950 | De Brocke | F25C 1/243 |
| | | | | | 426/104 |
| 3,214,128 | A | * | 10/1965 | Beck | F25C 1/243 |
| | | | | | D7/672 |
| 3,626,949 | A | | 12/1971 | Shute | |
| 6,360,387 | B1 | * | 3/2002 | Everhart | A47C 20/027 |
| | | | | | 5/490 |
| 7,695,489 | B2 | | 4/2010 | Brockman | |
| D627,055 | S | * | 11/2010 | Bain | D24/105 |
| 8,097,014 | B2 | | 1/2012 | Borkon | |
| 2004/0116955 | A1 | | 6/2004 | Foltz et al. | |

(Continued)

FOREIGN PATENT DOCUMENTS

| DE | 10310338 A1 * | 9/2004 | ............ A45D 40/00 |
| WO | WO 2016/040610 A1 | 3/2016 | |
| WO | WO 2017/004833 A1 | 1/2017 | |

(Continued)

OTHER PUBLICATIONS

Machine translation of DE-10310338-A1 dated Sep. 2004. (Year: 2004).*

(Continued)

*Primary Examiner* — Robert B Davis
(74) *Attorney, Agent, or Firm* — Crowell & Moring LLP (57) ABSTRACT

A kit for creating disposable dilators and a method for dilating using the kit are disclosed. The kit may include a plurality of disposable members fillable with an object and one or more components configured for facilitating shaping the plurality of disposable members into use configurations. Each of the plurality of disposable members may be configured to be shaped into one or more predetermined use configurations.

15 Claims, 9 Drawing Sheets

(56) References Cited

U.S. PATENT DOCUMENTS

2018/0071502 A1 3/2018 Hakim et al.

FOREIGN PATENT DOCUMENTS

WO    WO 2018/090014 A1    5/2018
WO    WO 2019/0175864 A1    9/2019

OTHER PUBLICATIONS

Reddit post entitled "Freezable dilators?" in the subreddit Vulvodynia, 3 pages posted Jul. 14, 2019 especially the comment by user "Shopenhauernoise". Retrieved from internet <reddit.com/c/vulvodynia/ccx4gy/freezable_dilators/?rdt=58935> (Year: 2019).*
Silicone Ice Cube Tray Green—Room Essentials™ _ Target, 6 pp., date unknown.
Source 14 Cavity Silicone Ice Cube Tray . . . Mold Mould with Cover on m.alibaba, 9pp., date unknown.
Wholesale 14 Cavities Non-Stick Hot Dog . . . Pan Ice Tray Mould From m.alibaba, 10pp. date unknown.
Buy Soul Source GRS dilator, The Pelvic Hub, 5pp., retrieved Oct. 30, 2019.
Cool Water Cones—Post Surgical Dilators—CMT Medical, 4pp., retrieved Oct. 28, 2019.
Frozen Condoms: Just What Your Battered Postpartum Vagina Ordered, BabyCenter, 8pp., retrieved Oct. 28, 2019.
Vaginal Dilators Vaginal Atropy Menopause Dilators, 3pp., retrieved Oct. 28, 2019.
How to Use a Vaginal Dilator after Radiation Treatment—A Patent Information Guide, 12pp., Jul. 2, 2015.

* cited by examiner

KIT FOR CREATING DISPOSABLE DILATORS AND METHOD FOR THE USE THEREOF

CROSS-REFERENCE TO RELATED APPLICATIONS

This patent application claims the benefit of U.S. Provisional Application No. 63/042,744, filed Jun. 23, 2020, the entirety of which is hereby fully incorporated by reference herein.

FIELD OF THE INVENTION

The present disclosure relates generally to a kit for creating disposable dilators, and methods for the use thereof.

BACKGROUND

Currently, vaginal dilators are used to stretch a user's vagina for treating vaginismus, gynecological cancer treatment side effects, and other medical conditions. Usually, the vaginal dilators are made from plastic, silicone, or stainless steel, which are difficult to use (e.g., insertion and removal) and/or clean in their home applications. The dilation process may be painful, and sometimes bleeding may occur. As such, washing the dilators before and after use may be time consuming.

In addition, usually only one dilator is given to a patient by the physician, such that when the patient needs larger sizes, the patient has to purchase them. As such, the patient may need to purchase dilators with different sizes multiple times when needed, which may cause inconvenience and interruption in the patient's dilation therapy.

SUMMARY

The present invention is defined by the following claims, and nothing in this section should be considered to be a limitation on those claims.

One general aspect of the present disclosure includes a kit for creating disposable dilators, including: a plurality of disposable members fillable with a fluid; and one or more components configured for facilitating shaping the plurality of disposable members into use configurations, where each of the plurality of disposable members is configured to be shaped into one or more predetermined use configurations.

Another general aspect of the present disclosure includes a kit for creating disposable dilators, including: a plurality of disposable members fillable with an object, the plurality of disposable members including a first disposable member and a second disposable member; and one or more components configured for facilitating shaping the plurality of disposable members into use configurations, where when the first and second disposable members are shaped into their respective use configurations, the first and second disposable members have different diameters.

Another general aspect of the present disclosure includes a method for dilating using a kit for creating disposable dilators, the kit including a plurality of disposable members fillable with a fluid and one or more components configured for facilitating shaping the plurality of disposable members into use configurations, each disposable member of the plurality of disposable members extending between an open end and a closed end, including: filing a first disposable member of the plurality of disposable members with a first predetermined amount of the fluid; placing the first disposable member filled with the first predetermined amount of the fluid in a freezer through the one or more components for a first predetermined amount of time such that the first predetermined amount of the fluid is frozen and the first disposable member filled with the first predetermined amount of the fluid is shaped into a first use configuration; sealing the open end of the first disposable member; inserting the closed end of the first disposable member into a cavity of a subject for a first desired depth; and removing the first disposable member from the cavity of the subject.

Another general aspect of the present disclosure includes a positional support for supporting a user in a dilation process, including a first wedge configured for supporting a user's back; and a second wedge configured for supporting a user's legs, where the second wedge includes a cutout facing the first wedge and configured for providing a space for using a dilator.

Another general aspect of the present disclosure includes a dilator, including a disposable member fillable with one or more objects; a first object configured to be filled into the disposable member; and a second object configured to be filled into the disposable member, where the first object has a substantially half cylindrical configuration, where the second object has a substantially half cylindrical configuration, and where when the first object and the second object both are filled into the disposable member, the disposable member has a substantially cylindrical configuration.

Another general aspect of the present disclosure includes a tray, having a plurality of grooves, including a first groove, a second groove, a third groove, and a fourth groove, where the first groove and the second groove have a same configuration, where the third groove and the fourth groove have a same configuration, and where the first and third grooves have different configurations.

The various embodiments of the kit for creating disposable dilators, and methods for the creation and use thereof, provide significant advantages over other dilators. For example and without limitation, the disclosed kit allows for quick and easy creation of one or more dilators (e.g., vaginal dilators) with different sizes that are disposable and simple to use, which may change size easily and reduce pain due to use of ice.

The foregoing paragraphs have been provided by way of general introduction, and are not intended to limit the scope of the following claims. The various preferred embodiments, together with further advantages, will be best understood by reference to the following detailed description taken in conjunction with the accompanying drawings.

DETAILED DESCRIPTION OF THE PRESENTLY PREFERRED EMBODIMENTS

It should be understood that the term "plurality," as used herein, means two or more. The terms "first," "second," and so on, as used herein are not meant to be assigned to a particular component so designated, but rather are simply referring to such components in the numerical order as addressed, meaning that a component designated as "first" may later be a "second" such component, depending on the order in which it is referred. It should also be understood that designation of "first" and "second" does not necessarily mean that the two components or values so designated are different, meaning for example a first disposable member may be the same as a second disposable member, with each simply being applicable to separate but identical components. The term "about" is specifically defined herein to include the specific value referenced as well as a dimension that is within 5% of the dimension both above and below the dimension.

A kit 10 for creating disposable dilators, such as vaginal dilators, is shown in FIGS. 1-7. While disposable vaginal dilators are specifically described herein, the kit 10 may be used to create disposable dilators for use in dilating other parts of a human body, including any orifice of a human body, such as anus, urethra, umbilicus, ear, nostril, and mouth. For the sake of brevity, the kit 10 disclosed herein is described and depicted as a kit for creating disposable vaginal dilators, one of ordinary skill in the art, with a thorough review of the subject specification and figures, would readily comprehend how the kit 10 may be used to create disposable dilators for use in dilating other parts of a human body, and would readily comprehend which other parts of a human body might be suitable without undue experimentation.

Figure 1:
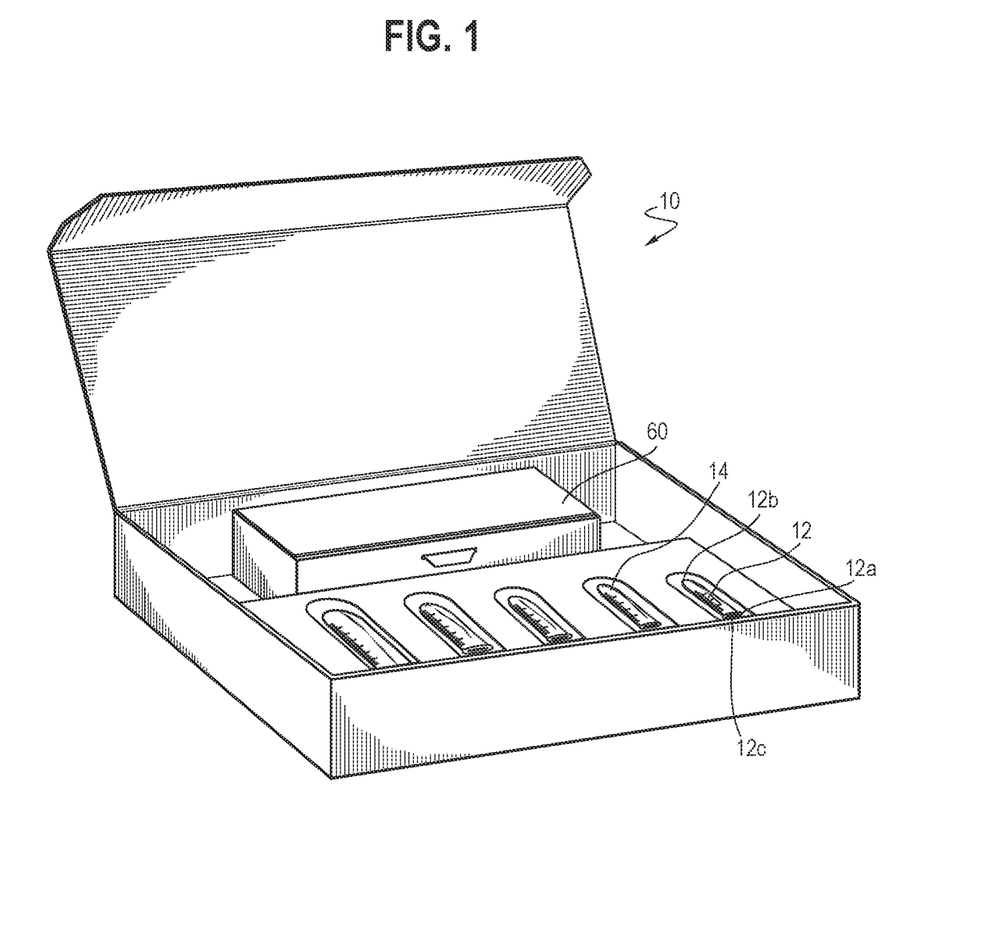
FIG. 1 is a schematic view of a kit for creating disposable dilators, in accordance with certain aspects of the present disclosure.

Referring to FIG. 1, the kit 10 may include a plurality of disposable members (e.g., five disposable members in their non-use configurations, as shown), including a first disposable member 12 and a second disposable member 14. The plurality of disposable members may be made of medical disposable glove materials, ultrasound cover materials, or other flexible medical disposable materials, such as polyurethane or polyethylene. Each disposable member may have an elongate configuration extending between an open end (e.g., open end 12a of the first disposable member 12) and a closed end (e.g., closed end 12b of the first disposable member 12), with a lumen (e.g., lumen 12c of the first disposable member 12) extending therethrough. The disposable members may be used to create disposable dilators, as discussed in greater detail below, which are simple to use, without the need for washing before and after use. In another embodiment, the first disposable member 12 may be configured as a plastic enclosure.

Figure 2:
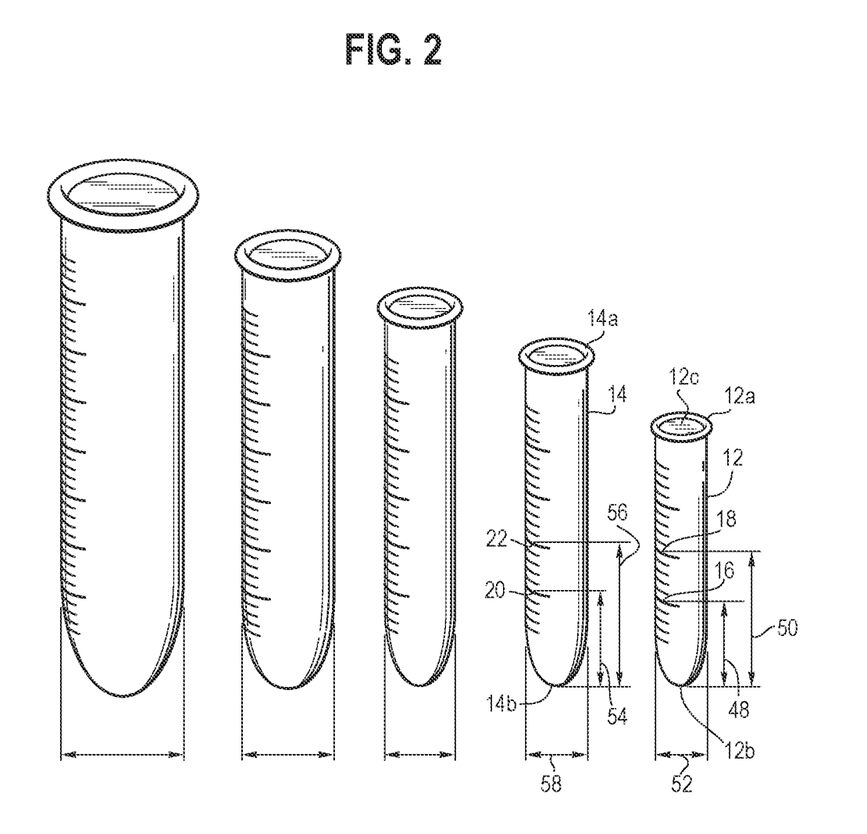
FIG. 2 is a schematic view of a plurality of disposable members configured for creating disposable dilators, in accordance with certain aspects of the present disclosure.
Figure 4:
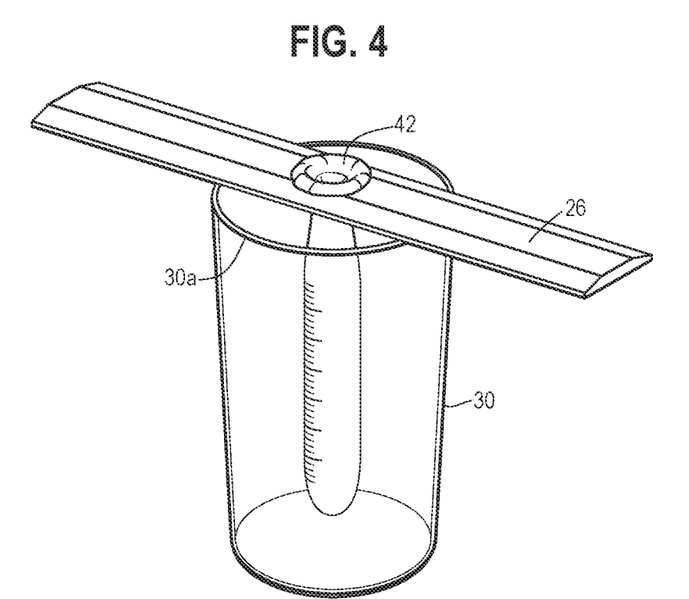
Figure 5:
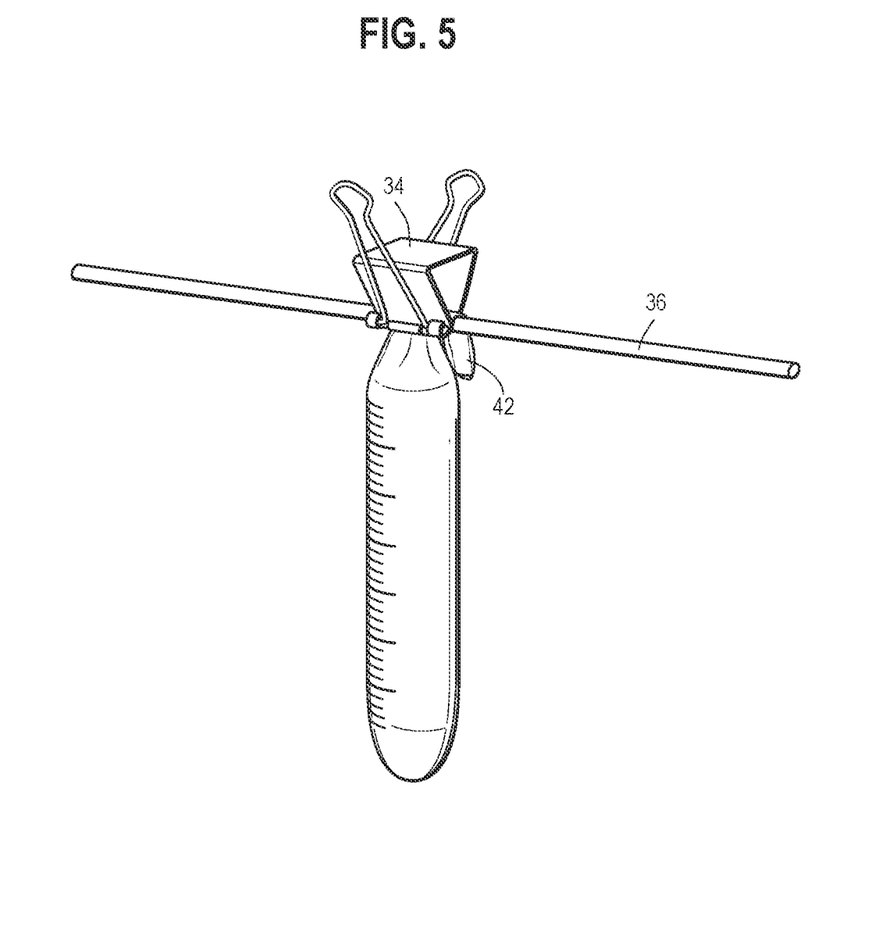
FIG. 5 is a schematic view of a second embodiment of a device configured for facilitating shaping the plurality of disposable members of FIG. 2 into use configurations of disposable dilators, in accordance with certain aspects of the present disclosure.

Each disposable member is fillable with an object (e.g., in the lumen) and may translate between a non-use configuration (e.g., when the disposable member is not filled with anything, as shown in FIG. 1) and a use configuration (e.g., when the disposable member is filled with an object, as shown in FIG. 2). In some embodiments, as shown in FIGS. 2, 4, and 5, each of the plurality of disposable members may have a substantially cylindrical configuration when in use configurations. In some embodiments, as shown in FIGS. 2, 4, and 5, the closed end of each disposable member (e.g., closed end 12b of the first disposable member 12) may have a dome shape configured for easy insertion of the disposable member into a female's vagina. In the embodiment of a plastic enclosure, the enclosure may have the same shape and interior volume in both the non-use and use configurations.

In some embodiments, each disposable member may be fillable with a fluid (e.g., water and thus ice after the water is frozen), tissue paper, cotton, silicone, molded forms, or other suitable objects, depending on the intended application. In some therapy applications (e.g., vaginal dilation), filling with ice may be advantageous for reducing pain during dilation due to the analgesic effects of cold (e.g., numb areas that might otherwise be painful), as well as for easy removal of the dilator after use due to the reduced size caused by melted ice. In other therapy applications (e.g., when ice/cryotherapy would be contraindicated), ice may not be necessary or desirable, the disposable member may be filled with tissue paper or molded forms, which allows the user to easily and quickly change the size of a dilator by changing the amount of tissue paper filled therein or changing the size of molded forms filled therein. Filling the disposable member with tissue paper or molded forms also provides texture, firmness, customizable form, and/or ease of use.

In some embodiments, when the plurality of disposable members are filled with the fluid (e.g., water), the plurality of disposable members may be shaped into respective use configurations of disposable dilators when the fluid (e.g., water) is frozen. In some embodiments, each disposable member may be configured to be shaped into one or more predetermined use configurations. As shown in FIG. 2, the plurality of disposable members each may include spaced-apart markers disposed along their respective lengths. As such, each of the plurality of disposable members may be configured to be shaped into different use configurations with same/different diameters and same/different lengths, depending on the location of the markers the fluid is filled to.

For example, the first disposable member 12 may have a first use configuration, with a first length 48, when filled with water (i.e., ice after frozen) to the first marker 16 and have a second use configuration, with a second length 50, when filled with water (i.e., ice after frozen) to the second marker 18, where the first and second use configurations may have the same diameter 52 while the second use configuration, with the second length 50, is longer than the first use configuration, with the first length 48. That is, the first disposable member 12 with the second use configuration can be advanced to a deeper location within a female's vagina for dilation. It will be appreciated that, in some embodiments, the second use configuration (e.g., filling water, and thus ice after frozen, to the second marker 18) may have a greater diameter than the first use configuration (e.g., filling water, and thus ice after frozen, to the first marker 16), depending on the flexibility of the material of the disposable member, without departing from the scope of the present invention.

In some embodiments, the plurality of disposable members, such as the first disposable member 12 and the second disposable member 14, may be configured to be shaped into different use configurations when filled with a same amount of the fluid (e.g., water, and thus ice after frozen). In some embodiments, the first and second disposable members 12 and 14 may be configured to be shaped into different use configurations with a same length and different diameters.

For example, the second disposable member 14 may have a first use configuration, with a first length 54, when filled with water (i.e., ice after frozen) to its first marker 20 and have a second use configuration, with a second length 56, when filled with water (i.e., ice after frozen) to its second marker 22, where the first and second use configurations of the second disposable member 14 may have the same diameter 58 while the second use configuration, with the second length 56, is longer than the first use configuration, with the first length 54. In some embodiments, when the first markers 16 and 20 of the first and second disposable members 12 and 14 have the same distance to their respective closed ends 12b and 14b (i.e., the first length 48 of the first disposable member 12 equals to the first length 54 of the second disposable member 14), the first use configurations of the first and second disposable members 12 and 14 may have the same length 48 or 54 (e.g., length of the ice disposed therein) while the first use configuration of the second disposable member 14 may have a greater diameter than the first use configuration of the first disposable member 12, when the diameter 58 of the second disposable member 14 is greater than the diameter 52 of the first disposable member 12.

It will be appreciated that the number of markers disposed along the length of each disposable member may be the same or different, and may be varied, as desired and/or needed, without departing from the scope of the present invention. The distance between each marker and the closed end of the respective disposable member may also be varied, as desired and/or needed, without departing from the scope of the present invention. In some embodiments, the distance between the first markers 16 and 20 of the first and second disposable members 12 and 14 and their respective closed ends 12b and 14b may be the same, while in other embodiments, the distance may be different.

It will be appreciated when the first and second disposable members 12 and 14 are filled with the same amount of fluid (e.g., water, and thus ice after frozen), the second disposable member 14 may have a use configuration with a greater diameter and a shorter length than the use configuration of the first disposable member 12. Use configurations with a smaller length and/or diameter may be used in initial stages of a dilation therapy and use configurations with a greater length and/or diameter may be used as dilation progresses, as discussed in greater detail below. Including a plurality of disposable members with different predetermined use configurations in the kit 10 allows a user to easily change the size of the disposable dilators, as desired and/or needed (e.g., as dilation progresses, a dilator with a greater length and/or diameter may be needed), by changing the amount of the fluid filled in the same disposable member or switching to another disposable member with a different predetermined use configuration (e.g., larger diameter).

While in FIG. 1, the kit 10 is shown to include five disposable members, it will be appreciated that the number of disposable members included in the kit 10 may be varied, as desired and/or needed, without departing from the scope of the present invention. The plurality of disposable members may be configured to be shaped into their respective use configurations with respective predetermined diameters. Some of the plurality of disposable members may be configured to have same use configurations (e.g., same diameters after ice formed therein) while some of the plurality of disposable members may be configured to have different use configurations (e.g., different diameters after ice formed therein). As one non-limiting example, disposable members with four different diameters in use configurations may be provided, with the four different diameters being about 1.5 cm, 2.25 cm, 3 cm, and 3.75 cm, respectively. As another non-limiting example, disposable members with five different diameters (e.g., as shown in FIG. 2) in use configurations may be provided, with the five different diameters being about 1.5 cm, 2 cm, 2.75 cm, 3.5 cm, and 4.25 cm, respectively.

The length of the plurality of disposable members included in the kit 10 may be the same or different, as desired and/or needed, without departing from the scope of the present invention, as long as the length of the disposable members is greater than a desired length of a use configuration (e.g., length of the ice formed therein), such that after the length of the use configuration is advanced into a female's vagina, the remaining length of the disposable member disposed outside the vagina allows for easy removal of the disposable member after use. In some embodiments, for example, the length of the disposable members may be between about 17 cm and about 23 cm.

Figure 6:
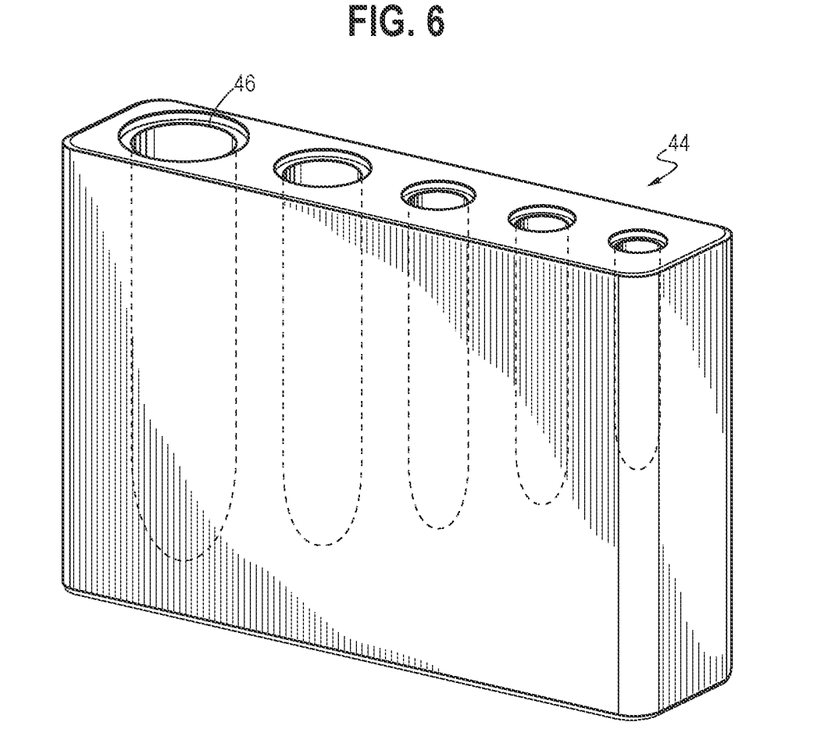
FIG. 6 is a schematic view of a third embodiment of a device configured for facilitating shaping the plurality of disposable members of FIG. 2 into use configurations of disposable dilators, in accordance with certain aspects of the present disclosure.
Figure 7:
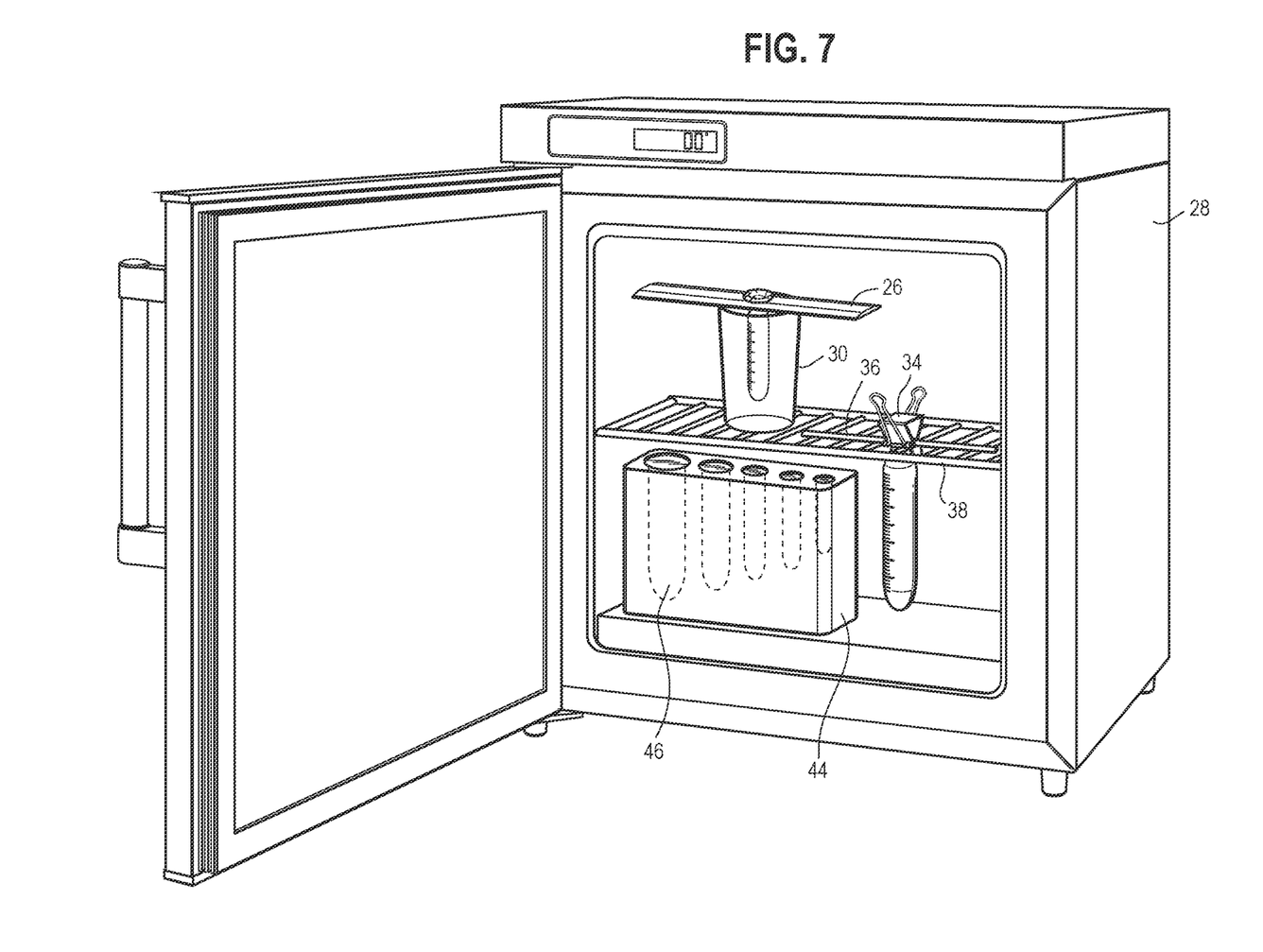
FIG. 7 is a schematic view of a freezer used in conjunction with the first, second, and third embodiments of the device, shown in FIGS. 3-6, to create disposable dilators, in accordance with certain aspects of the present disclosure.

Referring to FIGS. 1, 3-7, the kit 10 may also include one or more components 60 configured for facilitating shaping the plurality of disposable members into use configurations. In some embodiments, the one or more components 60 may be configured to hold the plurality of disposable members filled with the fluid (e.g., water) in a freezer. In some embodiments, as shown in FIGS. 3-5 and 7, the one or more components 60 may include at least one coupler (e.g., 24, 34) and at least one support member (e.g., 26, 36), where a coupler may be configured to secure one or more disposable members to a support member, such that when the support member is placed on a support structure (e.g., 30, 38) disposed in a freezer 28 (e.g., as shown in FIG. 7), the one or more disposable members (e.g., filled with the fluid) may extend downwardly, without encountering any obstructions, from the support member within the freezer 28 to form respective use configurations of disposable dilators (e.g., forming substantially cylindrical shape with a domed end after the fluid filled within the disposable members is frozen).

Figure 3:
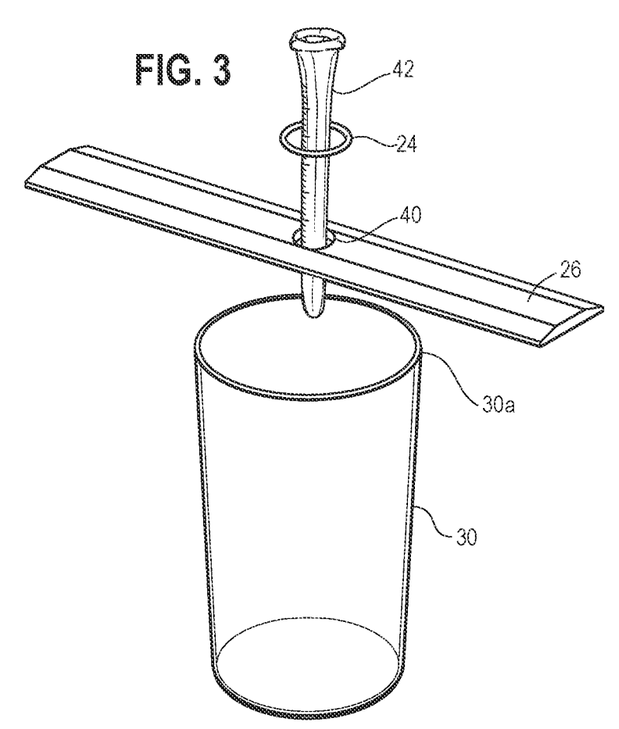
FIGS. 3-4 are schematic views of a first embodiment of a device configured for facilitating shaping the plurality of disposable members of FIG. 2 into use configurations of disposable dilators, in accordance with certain aspects of the present disclosure.

In some embodiments, as shown in FIGS. 3-4, the one or more components may further include a container 30 configured such that when the support member 26 is placed on an upper edge 30a of the container 30, the one or more disposable members (e.g., filled with the fluid) may extend downwardly, without encountering any obstructions, from the support member 26 within the container 30, such that after the fluid within the one or more disposable members is frozen, the one or more disposable members hanging down from the support member 26 may be shaped into use configurations of disposable dilators (e.g., substantially cylindrical shape with a domed end). In some embodiments, the support member (e.g., 26, 36) may be configured such that when it is placed on a shelf 38 of the freezer 28, the one or more disposable members (e.g., filled with the fluid and secured to the support member) may hang down from the support member 26 or 36 (also from the shelf 38), without encountering any obstructions, within the freezer and be shaped into use configurations of disposable dilators (e.g., substantially cylindrical shape with a domed end) after the fluid within the one or more disposable members is frozen.

In some embodiments, as shown in FIGS. 3 and 4, the coupler may be a ring 24 and the support member 26 may have an elongate configuration including one (e.g., as shown in FIG. 3) or more apertures 40 disposed along the length of the support member 26. In some embodiments, the ring 24 and the aperture 40 may be configured such that when the ring 24 is disposed on the support member 26 in registry with the aperture 40, a disposable member can extend through the ring 24 and the aperture (e.g., as shown in FIG. 3) with an upper end portion 42 of the disposable member wrapping around at least a portion of the ring 24 and extending between the ring 24 and an edge of the aperture 40 (e.g., as shown in FIG. 4) such that the disposable member (e.g., with the fluid filled therein) is secured to the support member 26 through the ring 24. In some embodiments, the diameter of the ring 24 may be slightly greater than the diameter of the aperture 40 and configured such that when the upper end portion 42 of the disposable member (e.g., with the fluid filled therein) wraps around a portion of the ring 24 and extends between the ring 24 and the edge of the aperture 40, the friction created between the ring 24, the upper end portion 42 of the disposable member, and the support member 26 is greater than the weight of the disposable member (e.g., with the fluid filled therein). In some embodiments, as shown in FIG. 5, the coupler may be a clip 34 configured for clipping the upper end portion 42 of one or more disposable members (e.g., with the fluid filled therein) and the support member 36 together, such that the one or more disposable members may be secured to the support member 36 and extend downwardly from the support member 36.

It will be appreciated that the number of couplers and support members provided in the kit 10 may be varied, as desired and/or needed, without departing from the scope of the present invention. It will be appreciated that one coupler may be configured to secure two or more disposable members to the support member (e.g., a clip with a length that allows for clipping multiple disposable members to the support member) and one support member (e.g., 26, 36) may be configured (e.g., with a sufficient length and load capacity) to support two or more disposable members (e.g., with the fluid filled therein), without departing from the scope of the present invention. It will be appreciated that different couplers may have different configurations configured for securing disposable members with different use configurations to the support member, without departing from the scope of the present invention.

For example, in some embodiments, as shown in FIGS. 3 and 4, the number of the rings 24 and apertures 40 disposed on the support member 26 may be varied, as desired and/or needed, without departing from the scope of the present invention. A support member 26 with a greater number of apertures 40 disposed thereon allows a greater number of disposable members to be shaped into their use configurations simultaneously (e.g., using a greater number of rings 24), which allows a user to prepare multiple disposable dilators at one time and take one to use whenever needed. In some embodiments, the apertures 40 disposed on the support member 26 may have different diameters, with the rings 24 having correspondingly different diameters, to accommodate the different diameters of the disposable members in use configurations. In some embodiments, when a plurality of support members 26 are provided, the apertures 40 disposed on each support member 26 may have the same diameter, while the apertures 40 disposed on different support members 26 may have different diameters. It will be appreciated that the configuration (e.g., shape, size) of the rings 24 and the apertures 40 may be varied, as desired and/or needed, without departing from the scope of the present invention, as long as a disposable member (e.g., filled with the fluid) may be secured to the support member 26 via the engagement between a ring 24 and a corresponding aperture 40.

In some embodiments, as shown in FIG. 6, the one or more components may include a mold 44 (e.g., silicone mold) having a plurality of vertical cavities 46 with the use configurations of the plurality of disposable members (e.g., substantially cylindrical shape with a substantially domed closed end). The term "vertical" is intended to describe the direction with respect to the plane the mold 44 is disposed upon (e.g., a flat surface in a freezer). Each vertical cavity 46 may be configured to hold one disposable member filled with the fluid (e.g., water) in the freezer such that after the fluid (e.g., water) filled within the disposable member is frozen, the disposable member is shaped into a desired use configuration (e.g., substantially cylindrical shape with a substantially domed closed end). In some embodiments, each vertical cavity 46 may be configured to hold fluid (e.g., water), directly placed therein, in the freezer such that after the fluid (e.g., water) is frozen, the frozen fluid (e.g., formed ice) has a desired use configuration (e.g., substantially cylindrical shape with a substantially domed end) and can be taken out of the vertical cavity 46 and be placed into a disposable member to form a disposable dilator. It will be appreciated that the number of vertical cavities 46 in the mold 44 may be varied, as desired and/or needed, allowing one or more disposable members to be shaped into use configurations simultaneously, and the vertical cavities 46 may have the same or different configurations (e.g., different diameters and/or lengths) to accommodate the different use configurations of the disposable members, without departing from the scope of the present invention.

In some embodiments, as shown in FIGS. 11-14, the one or more components may include a tray 72 having a plurality of grooves (e.g., a first groove 74, a second groove 76, a third groove 78, a fourth groove 80, a fifth groove 82, a sixth groove 84, a seventh groove 86, and an eighth groove 88, as shown in FIGS. 11-14) with varying configurations, where the plurality of grooves are configured for forming objects (e.g., ice, silicone) with varying configurations to be disposed in the plurality of disposable members for shaping the plurality of disposable members into varying use configurations of disposable dilators. The tray 72 may be made of silicone and/or plastic. In use, for example, a user may fill a desired amount of water into one or more of the plurality of grooves, and then put the tray 72 into a freezer. After the water is frozen, the formed ice may be taken out of the respective groove(s) and inserted into one or more disposable members such that disposable dilators with desired use configurations may be formed. Then the disposable dilators may be used in the same way in dilation processes as discussed in this application.

Figure 11:
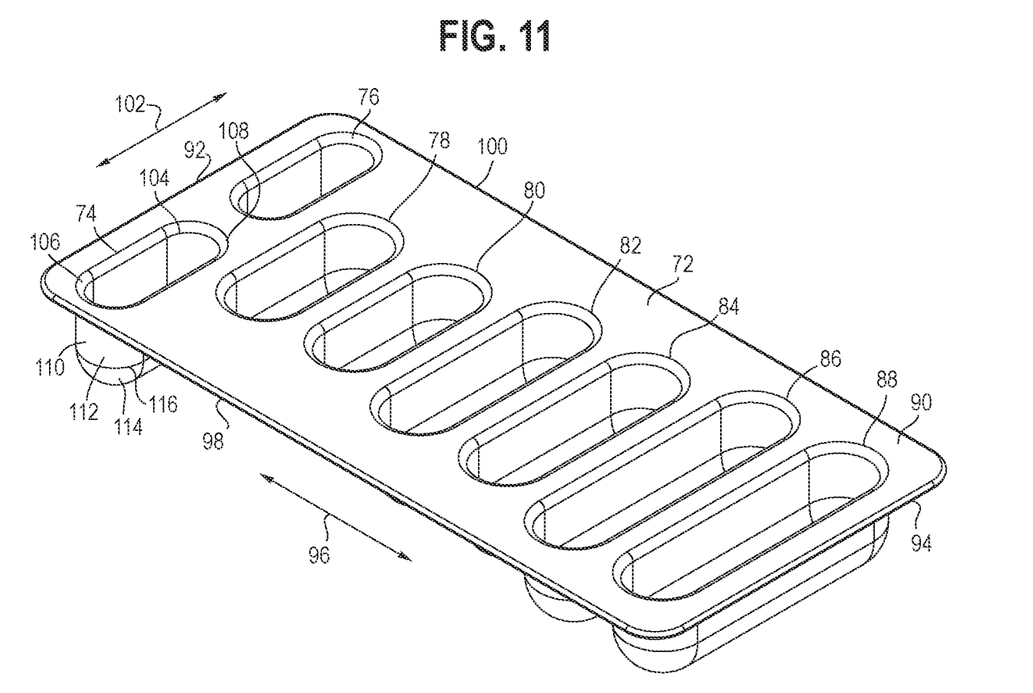
FIG. 11 is a schematic perspective view of a fourth embodiment of a device configured for facilitating shaping the plurality of disposable members of FIG. 2 into use configurations of disposable dilators, in accordance with certain aspects of the present disclosure.
Figure 12:
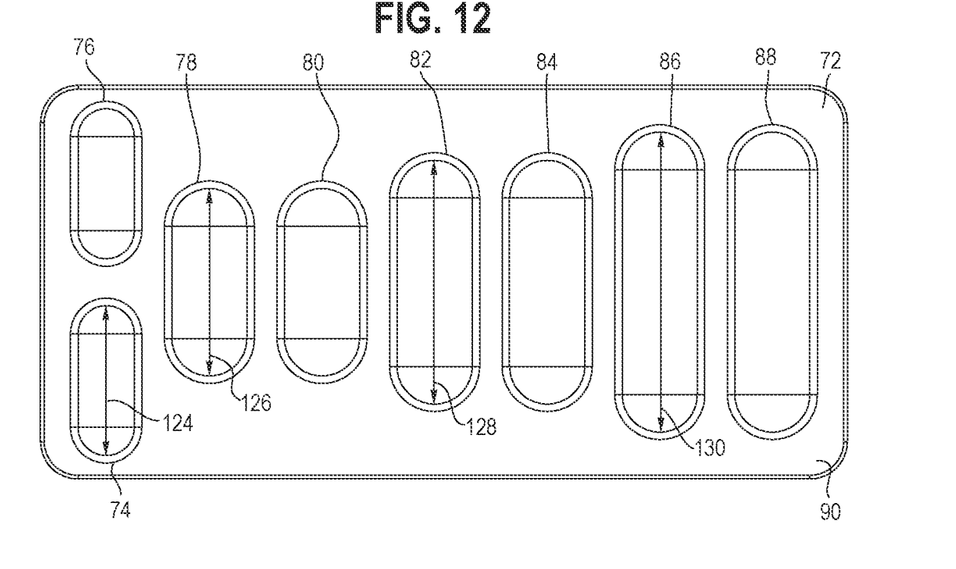
FIG. 12 is a schematic top view of the fourth embodiment of the device of FIG. 11.
Figure 13:
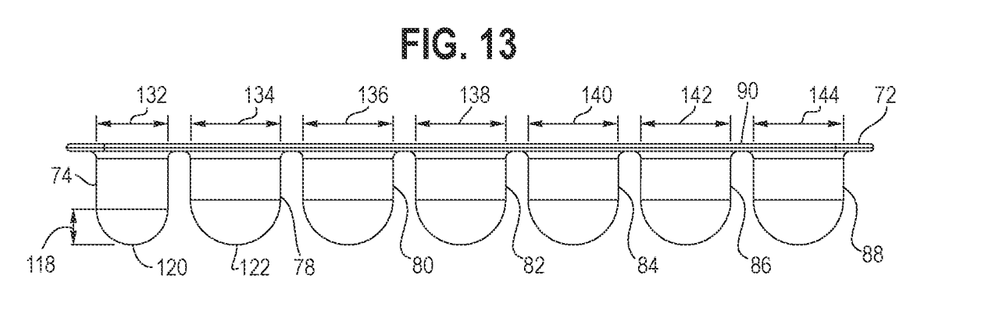
FIG. 13 is a schematic front view of the fourth embodiment of the device of FIG. 11.

In some embodiments, as shown in FIGS. 11-14, the tray 72 may have an upper surface 90 extending between a first edge 92 and a second edge 94 in a first direction 96 and extending between a third edge 98 and a fourth edge 100 in a second direction 102. The first direction 96 may be vertical to the second direction 102 in the plain of the upper surface 90. In some embodiments, some grooves (e.g., the first and second grooves 74 and 76) may be spaced apart in the second direction 102 (e.g., as shown in FIGS. 11-12). In some embodiments, some grooves (e.g., the third to the eighth grooves 78-88) may be spaced apart in the first direction 96 (e.g., as shown in FIGS. 11-13). In some embodiments, some of the plurality of grooves (e.g., grooves 78-88) may be spaced apart equidistant in the first direction 96 (e.g., as shown in FIGS. 12-13).

In some embodiments, as shown in FIGS. 11-14, the plurality of grooves may have similar/same shapes with varying dimensions. For example, as shown in FIG. 11, the first groove 74 includes a first opening 104 disposed on the upper surface 90 of the tray 72, where the first opening 104 extends a first length 124 in the second direction 102 between a first end 106 and a second end 108. The first and second ends 106 and 108 may be rounded (e.g., each end forming a half circle), and the remaining portion of the first opening 104 may be straight (e.g., extending in parallel with the first edge 92). The first groove 74 also includes a lower portion 110 including a first sidewall 112 extending downwardly (e.g., vertically downwardly relative to the upper surface 90 of the tray 72) from the first opening 104 and a first bottom wall 114 extending downwardly from a lower edge 116 of the first sidewall 112, forming a rounded or domed bottom surface. This configuration is advantageous for forming objects (e.g., ice, silicone) with predetermined configurations having curved/rounded/domed end/side surfaces.

With this configuration, in use, for example, a user may fill a fluid (e.g., water) into the first groove 74 to a desired depth to form a predetermined configuration of ice (when the water is frozen) with at least three rounded/curved/domed surfaces. Then the formed ice may be placed in a disposable member such that the disposable member is shaped into a predetermined use configuration (e.g., substantially partial cylindrical shape with at least three rounded/curved/domed surfaces). For example, when water is filled into the first groove 74 to a first depth 118 (as shown in FIG. 13), ice having a substantially half cylindrical shape with at least three rounded/curved/domed surfaces may be formed when the water is frozen.

Figure 14:
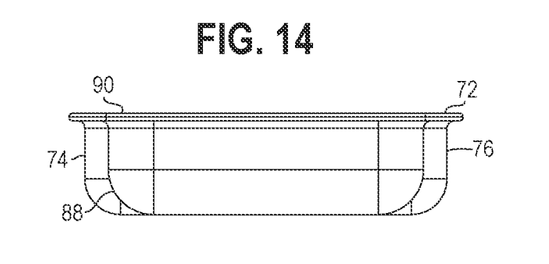
FIG. 14 is a schematic side view of the fourth embodiment of the device of FIG. 11.

In some embodiments, at least two grooves of the plurality of grooves may have the same configuration (e.g., same length, width, and depth). For example, as shown in FIGS. 12-14, the first and second grooves 74 and 76 have the same configuration, the third and fourth grooves 78 and 80 have the same configuration, the fifth and sixth grooves 82 and 84 have the same configuration, and the seventh and eighth grooves 86 and 88 have the same configuration. With this configuration, objects (e.g., ice, silicone) formed in the grooves with the same configuration may be used together for shaping a disposable member into a predetermined use configuration (e.g., two formed ice cubes with substantially half cylindrical shapes may be put together to form a substantially cylindrical shape with rounded/curved/domed surfaces). Accordingly, this configuration is advantageous as it allows for forming objects with bigger predetermined configurations using grooves with smaller dimensions.

For example, a user may use the tray 72 and a disposable member to form a disposable dilator, where the disposable dilator may include a disposable member fillable with one or more objects, a first object configured to be filled into the disposable member, and a second object configured to be filled into the disposable member, where the first object has a substantially half cylindrical configuration (e.g., formed by the first groove 74), where the second object has a substantially half cylindrical configuration (e.g., formed by the second groove 76), and where when the first object and the second object both are filled into the disposable member, the disposable member has a substantially cylindrical configuration.

In some embodiments, as shown in FIGS. 13 and 14, the plurality of grooves may have the same depth, where the lowest surfaces of the respective bottom walls of the plurality of grooves (e.g., the lowest surface 120 of the first groove 74 and the lowest surface 122 of the third groove 78) extend along a same surface that is in parallel with the upper surface 90 of the tray 72. With this configuration, the tray 72 may be securely placed on a plane surface without the need of other support. In some embodiments, some of the plurality of grooves may have different lengths configured to form objects (e.g., ice, silicon) with different use configurations of disposable dilators. For example, as shown in FIG. 12, the first length 124 of the first groove 74 may be smaller than the third length 126 of the third groove 78, the third length 126 of the third groove 78 may be smaller than the fifth length 128 of the fifth groove 82, and the fifth length 128 of the fifth groove 82 may be smaller than the seventh length 130 of the seventh groove 86. The lengths of the plurality of grooves may be varied, as desired and/or needed, to form objects (e.g., ice, silicone) with predetermined configurations. As one non-limiting example, the first, third, fifth, and seventh lengths may be about 4, 5, 6.5, and 8 centimeters, respectively.

It will be appreciated that the number and spacing of the plurality of grooves, and the length, width, depth, shape of each groove in the tray 72 may be varied, as desired and/or needed, allowing objects (e.g., ice, silicone) with varying use configurations to be formed simultaneously, to accommodate different use configurations of the disposable members, without departing from the scope of the present invention. As one non-limiting example, as shown in FIG. 13, the first groove 74 have a first width 132. The third to eighth grooves have respective third to eighth widths 134-144. The third to eighth widths 134-144 may be the same and may be greater than the first width 132. The first width 132 may be about 1.5 centimeter, and the third to eighth widths 134-144 each may be about 2 centimeters.

A method for dilating using the kit 10 described above will be discussed below. In some embodiments, a user may be provided with a kit 10 including a plurality of disposable members with different use configurations and one or more components 60 configured for facilitating shaping the plurality of disposable members into use configurations, as discussed above. The user may take a first disposable member 12 (e.g., with a relatively small diameter) out of the kit 10 and fill it with a first predetermined amount of a fluid (e.g., water). The user may then place the first disposable member 12 filled with the first predetermined amount of the fluid (e.g., water) in a freezer 28 through the one or more components 60 (as discussed above) for a first predetermined amount of time such that the first predetermined amount of the fluid is frozen and the first disposable member 12 filled with the first predetermined amount of the fluid is shaped into a first use configuration.

Then, the user may remove the first disposable member 12 from the one or more components 60 and the freezer 28 and seal the open end 12a of the first disposable member 12 (e.g., by making a knot at the open end 12a such that fluid will not come out during use). The user may then insert the closed end 12b of the first disposable member 12 into a cavity (e.g., vagina) of a human body for a first desired depth for dilation, with the sealed open end 12a of the first disposable member 12 disposed outside the cavity of the human body. Then, after a desired time and/or after the first predetermined amount of the fluid filled within the first disposable member 12 at least partially melts, the user may pull on the sealed open end 12a and remove the first disposable member 12 from the cavity of the human body and throw it away. It will be appreciated that the user may fill other objects within the disposable member and may shape multiple disposable members into use configurations of disposable dilators simultaneously, without departing from the scope of the present invention.

Figure 8:
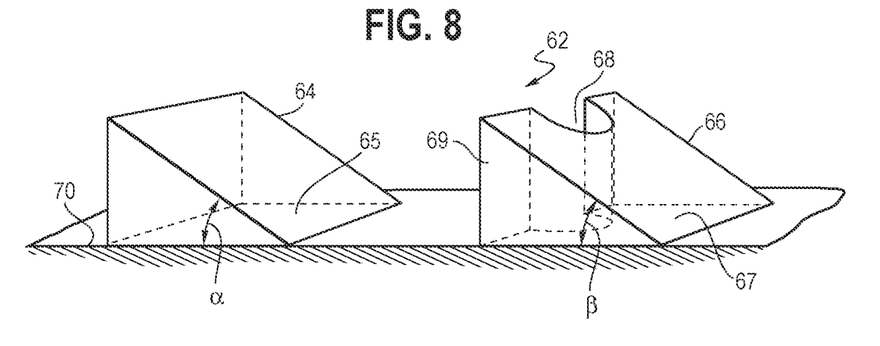
FIG. 8 is a schematic perspective view of a positional support in accordance with certain aspects of the present disclosure.
Figure 9:
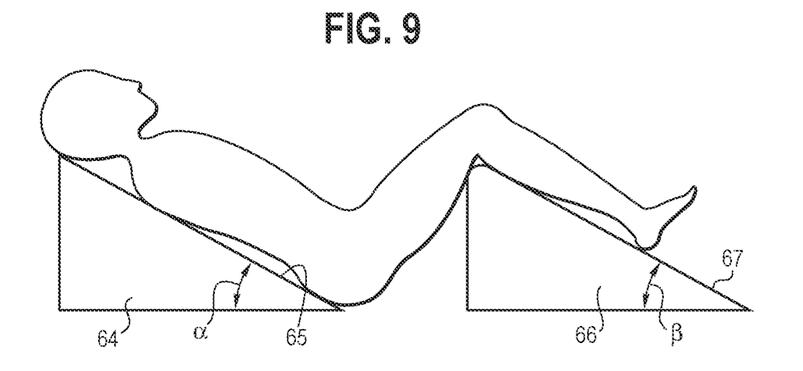
FIG. 9 is a schematic side view of the positional support of FIG. 8 during use, in accordance with certain aspects of the present disclosure.
Figure 10:
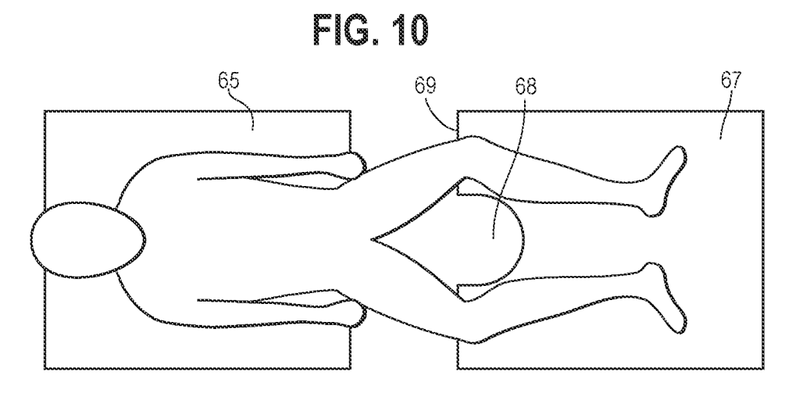
FIG. 10 is a schematic top view of the positional support of FIG. 8 during use, in accordance with certain aspects of the present disclosure.

In some embodiments, the user may use a positional support during the dilation process such that the body of the user may be supported in a suitable posture, which allows the user to position his or her body comfortably during dilation while being able to manipulate (e.g., insert a dilator into the body or remove a dilator from the body) the dilators easily. In some embodiments, as shown in FIGS. 8-10, a positional support 62 may include a first wedge 64 and a second wedge 66. The first and second wedges 64 and 66 may be made of any suitable materials that can provide both support and comfort to a user, such as foam. The first wedge 64 and the second wedge 66 may be spaced apart on a plane surface 70 such that a user may sit between the first and second wedges 64 and 66 and then lie down such that the user's back is supported by the first wedge 64 and the user's legs are supported by the second wedge 66.

In some embodiments, as shown in FIGS. 8 and 9, the first and second wedges 64 and 66 may have a substantially solid triangle configuration. The first wedge 64 may include a first sloping surface 65 (e.g., configured for supporting a user's back) that extends at a first angle $\alpha$ with respect to the plane surface 70 when the first wedge 64 is placed on the plane surface 70. The second wedge 66 may include a second sloping surface 67 (e.g., configured for supporting a user's legs) that extends at a second angle $\beta$ with respect to the plane surface 70 when the second wedge 66 is placed on the plane surface 70. The first and second angles $\alpha$ and $\beta$ may be the same or different, and may be any suitable angles, such as between about 15 degrees and about 60 degrees, as long as the first and second wedges 64 and 66 may provide comfort to the user during dilation. It will be appreciated, depending on the configuration of the user's body (e.g., length of the back, length of the legs), the angles $\alpha$ and $\beta$ may be varied, as desired and/or needed, to accommodate specific needs of a user, without departing from the scope of the present invention.

In some embodiments, as shown in FIGS. 8 and 10, the second wedge 66 may include a cutout 68 configured to face the cavity (e.g., vagina) of the user during use. The configuration of the cutout 68 may be varied, as desired and/or needed, as long as it provides a space for the user to easily insert the dilator into the cavity, position the sealed open end of the dilator disposed outside the cavity during dilation, and remove the dilator from the cavity after dilation, without departing from the scope of the present invention. For example, as shown in FIGS. 8 and 10, the cutout 68 may have a substantially half circle configuration extending along a side surface 69 of the second wedge 66.

As the dilation therapy progresses, such as when the user can insert one size of the use configuration of the disposable member completely into the cavity (e.g., vagina) without any discomfort, then the user may start using the next size up, either with the same diameter but greater length or with a larger diameter and same or greater length. For example, the user may fill a second disposable member 14 of the plurality of disposable members with a second predetermined amount of the fluid (e.g., water). Then the user may place the second disposable member 14 filled with the second predetermined amount of the fluid in a freezer 28 through the one or more components 60 (discussed above) for a second predetermined amount of time such that the second predetermined amount of the fluid is frozen and the second disposable member 14 filled with the second predetermined amount of the fluid is shaped into a second use configuration, where the second use configuration of the second disposable member 14 has a greater diameter and/or a greater length than the first use configuration of the first disposable member 12.

The user may then remove the second disposable member 14 from the one or more components 60 and the freezer 28 and seal the open end 14a of the second disposable member 14 (e.g., by making a knot at the open end 14a such that the fluid will not come out during use). The user may then insert the closed end 14b of the second disposable member 14 into the cavity (e.g., vagina) of a human body for a second desired depth for dilation (same as or different from the first desired depth), with the sealed open end 14a of the second disposable member 14 disposed outside the cavity of the human body. Then, after a desired time and/or after the second predetermined amount of the fluid filled within the second disposable member 14 at least partially melts, the user may pull on the sealed open end 14a and remove the second disposable member 14 from the cavity of the human body and throw it away.

As to the method of creating disposable dilators with desired use configurations, as one example, when the one or more components 60 include a support member (e.g., 26, 36) and a coupler (e.g., 24, 34), the user may secure a disposable member (e.g., 12, 14) to the support member through the coupler and then place the support member on a support structure (e.g., the container 30 or the shelf 38) disposed in the freezer 28 such that the disposable member (e.g., 12, 14) may extend downwardly from the support member within the freezer 28, without encountering any obstructions. As another example, when the one or more components 60 include a mold 44, the user may fill a disposable member (e.g., 12, 14) with the fluid (e.g., water) first and then place the disposable member (e.g., 12, 14) into the vertical cavity 46, or the user may fill the vertical cavity 46 with the fluid (e.g., water) first and then put the frozen fluid (e.g., ice) into a disposable member to achieve a desired use configuration of a disposable dilator.

Although the present invention has been described with reference to preferred embodiments, those skilled in the art will recognize that changes may be made in form and detail without departing from the spirit and scope of the invention. As such, it is intended that the foregoing detailed description be regarded as illustrative rather than limiting and that it is the appended claims, including all equivalents thereof, which are intended to define the scope of the invention.

What is claimed is:

1. A kit for creating disposable dilators, comprising:
a plurality of disposable members fillable with a fluid; and one or more components configured for facilitating shaping the plurality of disposable members into use configurations,
wherein each of the plurality of disposable members is configured to be shaped into one or more predetermined use configurations, and
wherein the one or more components comprises a tray having a plurality of grooves with varying configurations, and wherein the plurality of grooves are configured for forming objects with varying configurations to be disposed in the plurality of disposable members for shaping the plurality of disposable members into varying use configurations.

2. The kit of claim 1, wherein the fluid is water.

3. The kit of claim 1, wherein when the plurality of disposable members are filled with the fluid, the plurality of disposable members are shaped into respective use configurations when the fluid is frozen.

4. The kit of claim 1, wherein the plurality of disposable members each include spaced-apart markers disposed along their respective lengths.

5. The kit of claim 1, wherein each of the plurality of disposable members is configured to be shaped into different use configurations with a same diameter and different lengths.

6. The kit of claim 1, wherein the plurality of disposable members include a first disposable member and a second disposable member, and wherein the first and second disposable members are configured to be shaped into different use configurations when filled with a same amount of the fluid.

7. The kit of claim 6, wherein the first and second disposable members are configured to be shaped into different use configurations with a same length and different diameters.

8. The kit of claim 1, further comprising a first wedge adapted to support a back of a user and a second wedge adapted to support legs of the user.

9. The kit of claim 8,
wherein the second wedge includes a cutout facing the first wedge and configured for providing a space for using a dilator.

10. The kit of claim 8, wherein the first wedge and the second wedge have a substantially solid triangle configuration.

11. The kit of claim 9, wherein the cutout of the second wedge has a substantially half circle configuration extending along a side surface of the second wedge.

12. The kit of claim 1,
wherein the plurality of grooves of the tray comprises a first groove, a second groove, a third groove, and a fourth groove,
wherein the first groove and the second groove have a same configuration,
wherein the third groove and the fourth groove have a same configuration, and
wherein the first and third grooves have different configurations.

13. The kit of claim 12, wherein the first groove and the third groove have a same depth.

14. The kit of claim 12, wherein the first groove has a first length, the third groove has a third length, and the third length is greater than the first length.

15. The kit of claim 12, wherein the first groove has a first width, the third groove has a third width, and the third width is greater than the first width.

* * * * *